United States Patent [19]

Queuille et al.

[11] 4,120,946
[45] Oct. 17, 1978

[54] PHARMACEUTICAL COMPOSITIONS FOR BARIUM OPACIFICATION AND METHOD OF PREPARING THEM

[76] Inventors: André Queuille, 93, rue Denfert-Rochereau, 93130 Noisy-le-Sec; Francoise Herbemont, 10 La Renardiere, 1, rue Jean-Jaures, 93470 Coubron, both of France

[21] Appl. No.: 799,163

[22] Filed: May 23, 1977

[30] Foreign Application Priority Data

May 26, 1976 [FR] France .................. 76 15975

[51] Int. Cl.$^2$ .............................................. A61K 29/02
[52] U.S. Cl. ........................................................ 424/4
[58] Field of Search ............................................. 424/4

[56] References Cited

U.S. PATENT DOCUMENTS

| 3,539,682 | 11/1970 | Eriksson | 424/4 |
| 3,733,400 | 5/1973 | Queuille et al. | 424/81 |

FOREIGN PATENT DOCUMENTS 1,128,922  10/1968  United Kingdom .................. 424/4

Primary Examiner—Frederick E. Waddell
Attorney, Agent, or Firm—Stevens, Davis, Miller & Mosher

[57] ABSTRACT

The invention is directed to a pharmaceutical composition for barium opacification of the digestive tract, comprising colloidal barium sulfate and a polyacrylamide in an aqueous vehicle, and a method of preparing the same.

8 Claims, No Drawings

PHARMACEUTICAL COMPOSITIONS FOR BARIUM OPACIFICATION AND METHOD OF PREPARING THEM

The present invention relates to pharmaceutical compositions for barium opacification of the digestive tract as well as a method of preparing the same.

Since studies carried out at the start of the 20th century on the opacity of various substances to X-rays it has been known that in order to take X-rays of the digestive system it is advisable to use oxides or salts of metals of high atomic weight.

Thus derivatives of bismuth and, in particular, bismuth sub-nitrate, were initially selected for the taking of X-rays of the digestive tract.

As a result of numerous cases of poisoning, bismuth subnitrate was replaced by bismuth carbonate and then by oxides of metals of high atomic weight such as thorium oxide. These latter oxides were rather promptly abandoned due to particularly harmful secondary effects.

In about 1911, the use of barium sulfate was then recommended. As compared with the previous products, this latter salt had the advantage of great insolubility, great stability, and great chemical inertia towards reagents, which properties prevent its conversion into toxic soluble salts. Barium sulfate furthermore had the advantage of being low in cost.

Barium sulfate, on the other hand, had the drawback that it was difficult to maintain it in suspension; thus it was first of all attempted to produce it in a very finely divided state and then to place it in suspension in as viscous a vehicle as possible.

A number of preparations were carried out along this line. Thus one may in particular cite "Chemical Abstract 28, page 3195/1 (1934)" which describes the preparation of a gum tragacanth mucilage which maintains the barium sulfate in suspension. Numerous other preparations have been described in the literature.

These preparations generally seek to combine good suspension of the barium sulfate with good adherence to the walls of the organs to be X-rayed. It is known that insufficient adherence will make it impossible to obtain X-ray pictures of high precision.

It is furthermore preferable to be able to dilute the preparations as required for the specific needs. This cannot always be done with the preparations known up to the present time.

The applicant has thus sought to prepare new compositions for barium opacification of the digestive tract which do not present the aforementioned drawbacks, and it has been found that this problem can be solved by using, in particular, polyacrylamides, the use of which as a protective agent for the gastric mucosa is disclosed in U.S. Pat. No. 3,733,400 issued May 15, 1973.

The object of the present invention is therefore to provide pharmaceutical compositions for barium opacification of the digestive tract which are characterized by the fact that they contain colloidal barium sulfate and a polyacrylamide in an aqueous vehicle.

In accordance with the invention, the pharmaceutical compositions described above are advantageously characterized by the fact that the polyacrylamide is nonionic and of high molecular weight.

By polyacrylamide of high molecular weight there is meant a product whose molecular weight is about 1,000,000 or greater.

Among the polyacrylamides as defined above, one may use, for example, the polyacrylamides marketed by DOW CHEMICAL under the registered trademarks "Separan NP 10", "Separan NP 20" or "Purifloc N 17". One may also advantageously employ the polyacrylamides marketed by NOBEL-HOECHST Chimie under the name "Bozefloc PL 2169" which is a nonionic polyacrylamide having a molecular weight of about 1,000,000 and a viscosity of about 150 cPo (c = 1% in water at pH = 7 and room temperature).

These water-soluble polyacrylamides have the advantage that, in low concentrations, they form viscous solutions which make it possible to maintain the barium sulfate in suspension and at the same time permit good adherence of the preparation to the walls of the organs which it is desired to X-ray.

In accordance with the invention, the polyacrylamide content is advantageously between 0.1% and 5% of the barium sulfate content. A polyacrylamide content of about 0.5% of the barium sulfate content is preferred.

In accordance with the invention, the aqueous vehicle advantageously consists of distilled water, to which a conventional antiseptic agent may have been added. The aqueous vehicle makes it possible to form, with the polyacrylamide, an aqueous gel of high viscosity which maintains the barium sulfate in suspension.

Under the preferred conditions of the invention, the compositions advantageously contain one part of polyacrylamide gel of a polyacrylamide content varying between 0.1% and 5% to one to two parts of colloidal barium sulfate.

The preferred pharmaceutical compositions of the invention contain one part of approximately 0.7% polyacrylamide gel to 1.4 part of colloidal barium sulfate.

The antiseptic agent is one customarily used in Galenic pharmacy. Among those which may be used, for instance, are methyl parahydroxybenzoate, ethyl parahydroxybenzoate, or propyl parahydroxybenzoate. The antiseptic agent may also be an acid, such as benzoic acid or sorbic acid, or alkaline salts of said acids. The antiseptic agent is used in customary proportions.

The pharmaceutical compositions of the present invention may furthermore contain a thickening agent. Such a thickening agent may consist of gelatin or of cellulose ethers, such as the hydroxy-ethyl cellulose marketed by Hercules Powder Co. Ltd. under the registered trademark "Natrosol 250", or of sodium carboxymethylcellulose.

The thickening agent may also consist of polysaccharides, such as the products Aubygel X 52, Lygomme and Satiagel marketed by Pierrefitte-Auby, Rhodigel 23, marketed by Rhone Poulenc, or Kelzan marketed by Kelco Company. The thickening agent is used in customary proportions.

The pharmaceutical compositions of the present application may also advantageously contain an antifoaming agent. The antifoaming agent may consist of a food-grade silicone such as the product marketed by Rhone Poulenc under the name Silicone Antifoam 30.

Pharmaceutical compositions in accordance with the invention, as described above, have remarkable opacifying properties for X-rays and very good adherence to the walls of the organs which it is desired to X-ray.

These compositions furthermore have the advantage that they can be diluted as desired in accordance with the requirements under conditions compatible with use without thereby losing their physical properties.

Due to these remarkable opacifying properties, the compositions of the present invention can be used for radioscopy, radiography, or radiocinematography in examinations requiring, for instance, opacification of the pharynx, of the esophagus, of the stomach, of the duodenum, or of the colon, in order to detect functional or kinetic organic anomalies.

The ordinary dose, which varies in accordance with the composition employed, the subject treated, the organ to be X-rayed and the manner of administration may, for instance, be an amount which assures the ingestion of 140 g of colloidal barium sulfate orally in man.

These compositions may be used as is, or drinking water, for instance 1 to 3 volumes thereof, may be added to them.

Another object of the invention is a method of preparing the pharmaceutical compositions described above which is characterized by preparing an aqueous gel of polyacrylamide and an aqueous vehicle, incorporating the resultant gel into screened colloidal barium sulfate, possibly adding a thickening agent and an antifoaming agent, homogenizing, and making up to the desired volume by the addition of the aqueous vehicle.

The pharmaceutical compositions of the invention are intended for oral or rectal administration.

These compositions, which are in the form of gels, may contain, in addition to the components mentioned above, also stabilizers and preservatives, as well as sweetening or flavoring agents. However, it should be pointed out here that these sweetening or flavoring agents must be sufficiently neutral so as not to result in secretion by the organs which it is desired to X-ray. These various agents may be incorporated in the composition upon the introduction of the thickening agent and the antifoaming agent.

Examples of the invention will now be described below by way of illustration and not of limitation.

EXAMPLE 1

Thirty doses were prepared of a barium suspension intended for oral administration, having the following formula per dose:

| | |
|---|---|
| colloidal barium sulfate | 140 g |
| hydroxy-ethylcellulose (Natrosol 250 KR) | 0.5 g |
| glycerine | 20 g |
| food grade silicone (Silicone Antifoam 30) | 1 g |
| tromethamine | 2.5 g |
| citric acid q.s. pH = 8 | |
| polyacrylamide (Bozefloc PL 2169) | 1.5 g |
| methyl parahydroxybenzoate | 0.110 g |

(1) Preparation of the solutions:
 (a) The methyl parahydroxybenzoate and the propyl parahydroxybenzoate are dissolved in about 2200 cc of distilled water;
 (b) The hydroxy-ethylcellulose is dissolved in a part of the solution obtained under (a) above;
 (c) The tromethamine and the sweetening agent are dissolved in another portion of the solution obtained in a) above;
 (d) The polyacrylamide (Bozefloc PL 2 169, Nobel Hoechst Chimie) is dissolved in the largest portion of the solution obtained under a) above;
 (e) The flavoring agent is incorporated in a few milliliters of solution obtained under a) above;
 (f) A 6 N citric acid solution is prepared with distilled water.

(2) Preparation of the barium suspension:
Into a tared receptacle there are introduced, in succession, 4200 g of screened colloidal barium sulfate, the solution of tromethamine and sweetening agent prepared under (c) above, the Silicone Antifoam 30 (Rhone-Poulenc) which is then agitated to form the barium sulfate into a paste, whereupon the solution prepared under (e) containing the flavoring agent is introduced.

There are then added in succession, homogenizing after each addition; the glycerin, the hydroxy-ethylcellulose gel prepared under (b) above, the polyacrylamide gel prepared under (d) above, and a part of the solution prepared under (a).

The mixture is homogenized, the pH adjusted to 8 by means of the citric acid solution, and completed with the rest of the solution prepared under (a), and then with a small amount of distilled water in order to obtain a total weight of 7200 g.

After homogenization, the preparation is divided into 30 doses of 240 g each. At the time of use, each does may be diluted by adding at least 100 ml of drinking water.

EXAMPLE 2

Ten doses were prepared of a barium suspension intended for rectal administration, each dose having the following formula:

| | |
|---|---|
| colloidal barium sulfate | 385 g |
| hydroxy-ethylcellulose (Natrosol 250 KR) | 1.375 g |
| glycerin | 55 g |
| food grade silicone (Silicone Antifoam 30) | 2.75 g |
| tromethamine | 6.875 g |
| citric acid q.s. pH = 8 | |
| polyacrylamide (Bozefloc PL 2169) | 8.25 g |
| methyl parahydroxybenzoate | 0.302 g |
| propyl parahydroxybenzoate | 0.060 g |
| aqueous excipient q.s.p. | 660 g |

Operating in the same manner as indicated in Example 1 but without adding sweetening agent or flavoring agent, 6600 g of a barium sulfate suspension were prepared, which was divided, after homogenization, into 10 doses having the formula indicated above.

At the time of use each dose can be diluted by adding at least 1000 ml of drinking water.

EXAMPLE 3

Thirty doses were prepared of a barium suspension intended for oral administration, each dose having the following formula:

| | |
|---|---|
| colloidal barium sulfate | 140 g |
| gelatin | 0.250 g |
| polyacrylamide (Bozefloc PL 2169) | 0.700 g |
| food grade silicone (Silicone Antifoam 30) | 0.250 g |
| methyl parahydroxybenzoate | 0.150 g |
| propyl parahydroxybenzoate | 0.030 g |
| sweetened flavored aqueous excipient q.s.p. | 240 g |

(1) Preparation of the solutions:
 (a) The methyl parahydroxybenzoate and the propyl parahydroxybenzoate are dissolved in about 2200 cc of distilled water;
 (b) The gelatin is dissolved in a part of the solution obtained under a) above;
 (c) The polyacrylamide (Bozefloc PL 2169, Nobel Hoechst Chimie) is dissolved in another portion of the solution obtained under a) above;

(d) The sweetening agent and the flavoring agent are dissolved in a few milliliters of the solution obtained under (a) above.

(2) Preparation of the barium suspension:

Into a tared receptacle there are introduced in succession the gelatin solution obtained under (b), the polyacrylamide gel obtained under (c), the solution containing the sweetening agent and the flavoring agent, and then the Silicone Antifoam 30 (Rhone-Poulenc) and the major part of the balance of the solution obtained under (a). The solution is warmed and homogenized; 4200 g of screened colloidal barium sulfate are wetted progressively by the resultant mixture; it is again homogenized, and the balance of the solution obtained under (a) is incorporated. It is made-up to 7200 g by addition of distilled water and homogenized, and the preparation is then divided into 30 doses of 240 g each.

At the time of use, each dose can be diluted by the addition of at least 100 ml of drinking water.

EXAMPLE 4

Ten doses of a barium suspension intended for rectal adminstration were prepared having the following formula per dose:

| | |
|---|---|
| colloidal barium sulfate | 385 g |
| gelatin | 0.687 g |
| polyacrylamide (Bozeflec PL 2169) | 1.925 g |
| food grade silicone (Silicone Antifoam 30) | 0.687 g |
| methyl parahydroxybenzoate | 0.412 g |
| propyl parahydroxybenzoate | 0.082 g |
| aqueous excipient q.s.p. | 660 g |

Operating in the same manner as indicated in Example 3 but without adding sweetening agent or flavoring agent, 6600 g of a barium sulfate suspension were prepared, which was divided, after homogenization, into 10 doses having the formula indicated above.

At the time of use, each dose may be diluted by the addition of at least 1000 ml of drinking water.

EXAMPLE 5

Thirty doses of a barium suspension intended for oral administration were prepared, having the following formula per dose:

| | |
|---|---|
| colloidal barium sulfate | 140 g |
| polyacrylamide (Bozefloc PL 2169) | 0.700 g |
| food grade silicone (Silicone Antifoam 30) | 0.250 g |
| methyl parahydroxybenzoate | 0.150 g |
| propyl parahydroxybenzoate | 0.030 g |
| sweetened, flavored aqueous excipient q.s.p. | 240 g |

(1) Preparation of the solutions:
  (a) The methyl parahydroxybenzoate and the propyl parahydroxybenzoate are dissolved in about 2200 cc of distilled water;
  (b) The polyacrylamide (Bozefloc PL 2169, Nobel Hoechst Chimie) is dissolved in a part of the solution obtained under a) above;
  (c) The sweetening agent and the flavoring agent are dissolved in a few milliliters of the solution obtained under a) above.

(2) Preparation of the barium suspension:

Into a tared receptacle there are introduced in succession the polyacrylamide gel, the solution containing the sweetening agent and the flavoring agent, and then the Silicone Antifoam 30 (Rhone-Poulenc) and the major part of the balance of the solution obtained under (a). The mixture is warmed and homogenized, and 4200 g of screened colloidal barium sulfate are progressively wetted by the mixture obtained; thereupon it is again homogenized and the balance of the solution obtained under (a) is incorporated. It is made up to 7200 g by the addition of distilled water, and then homogenized, whereupon the preparation is divided into 30 doses of 240 g each.

At the time of use each dose may be diluted by adding at least 100 ml of drinking water.

EXAMPLE 6

Ten doses were prepared of a barium suspension intended for rectal administration, each dose having the following formula:

| | |
|---|---|
| colloidal barium sulfate | 385 g |
| polyacrylamide (Bozefloc PL 2169) | 1.925 g |
| food grade silicone (Silicone Antifoam 30) | 0.687 g |
| methyl parahydroxybenzoate | 0.412 g |
| propyl parahydroxybenzoate | 0.082 g |
| aqueous excipient q.s.p. | 660 g |

Operating in the same manner as indicated in Example 5 but without the addition of sweetening agent or flavoring agent, 6600 g were prepared of a barium sulfate suspension which was divided, after homogenization, into 10 doses having the formula indicated above.

At the time of use, each dose can be diluted by the addition of at least 1000 ml of drinking water.

Clinical Study (A) Study record

The various preparations were subjected to various radiological studies in succession. The compositions to be studied and the characteristics of the X-ray pictures obtained were analyzed, using the same parameters for each of the tests.

The products before ingestion were evaluated on basis of the following parameters:
-appearance of the preparation;
-handling;
-dilution;
-foam;
-homogeneity;
-sedimentation;
-taste.

The quality of the X-rays was evaluated by the following parameters:
-opacity;
-adherence to the mucosa;
-bubbles;
-grain;
-sedimentation;
-digestive secretions;
-evacuation.

Each parameter was the object of a quantitative evaluation expressed in the form of crosses: one cross indicates poor or mediocre results, two crosses average results, three crosses good results, and four crosses very good results.

An overall evaluation taking into consideration all of the parameters was also made by the investigator.

(B) Tests carried out (a) The compositions prepared in Examples 3 and 5 were administered orally, after dilution at the time of use with drinking water to a volume varying from 300 to 500 ml. These compositions are referred to below as compositions A and B respectively.

X-rays of the stomach were taken.

(b) The compositions prepared in Examples 4 and 6 were administered in the form of enemas, after dilution at the time of use with drinking water to a volume varying from 2000 to 2800 ml.

These compositions are referred to hereinbelow as compositions C and D respectively.

X-rays of the colon were taken.

(C) Results (a) In Table 1 below there have been entered the observations made with respect to the absence of bubbles, the fineness of the grain, the adherence to the mucosa, the absence of hypersecretion, as well as the overall result:

TABLE 1

| Composition Studied | Absence of Bubbles | Fineness of grain | Adherence to the mucosa | Absence of hyper-secretion | Overall Result |
|---|---|---|---|---|---|
| A | ++++ | +++ | +++ | ++++ | +++ |
| A | ++++ | +++ | +++ | ++++ | +++ |
| A | ++++ | +++ | ++ | ++++ | ++ to +++ |
| A | ++++ | +++ | +++ | ++++ | +++ |
| A | ++++ | ++++ | ++++ | ++++ | ++++ |
| B | ++++ | ++++ | ++++ | ++++ | ++++ |
| B | ++++ | ++++ | ++++ | ++++ | ++++ |
| B | ++++ | ++++ | ++++ | ++++ | ++++ |
| B | ++++ | ++++ | ++++ | ++++ | ++++ |
| B | ++++ | ++++ | ++++ | ++++ | ++++ |

For all the other parameters of the test record indicated under (A) above, the results were found to be excellent.

These results show, in particular, that composition B gives very good X-rays of the stomach;

(b) In Table 2 below, there have been entered the observations made as to the absence of bubbles, the fineness of the grain, the adherence to the mucosa, the absence of hypersecretion, as well as the overall result:

TABLE 2

| Composition Studied | Absence of Bubbles | Fineness of grain | Adherence to the mucosa | Absence of hyper-secretion | Overall Result |
|---|---|---|---|---|---|
| C | ++++ | ++++ | ++++ | ++++ | ++++ |
| C | ++++ | ++++ | ++++ | ++++ | ++++ |
| C | ++++ | ++++ | ++++ | ++++ | ++++ |
| C | ++++ | ++++ | ++++ | ++++ | ++++ |
| C | ++++ | ++++ | ++++ | ++++ | ++++ |
| D | ++++ | ++++ | ++++ |  | ++++ |
| D | ++++ | ++++ | ++++ |  | ++++ |
| D | ++++ | ++++ | ++++ | ++++ | ++++ |
| D | ++++ | ++++ | ++++ |  | ++++ |
| D | ++++ | ++++ | ++++ |  | ++++ |

For the other parameters of the study record indicated under (A) above, the results were found to be excellent. However, it should be noted that the absence of hypersecretion was not noted in four of the five observations carried out with composition D.

These results show in particular that compositions C and D give very good X-rays of the colon.

(D) Conclusions

The results obtained show that the compositions studied are excellent for radiographic study of the digestive tract.

These compositions, in particular, have the advantage of possessing very good adherence and of being capable of being diluted as desired in order to examiner all parts of the digestive tract.

What is claimed is:

1. A pharmaceutical composition for barium opacification of the digestive tract, comprising colloidal barium sulfate and a polyacrylamide having a molecular weight of at least about one million in an aqueous vehicle, the polyacrylamide content being between 0.1% and 5% of the barium sulfate content.

2. A composition according to claim 1, wherein the polyacrylamide is nonionic.

3. A composition according to claim 1, wherein the aqueous vehicle is formed of distilled water.

4. A composition according to claim 3 wherein an antiseptic agent has been added to the aqueous vehicle.

5. A composition according to claim 1 containing a thickening agent.

6. A composition according to claim 1 containing an antifoaming agent.

7. A method of preparing a pharmaceutical composition as defined in claim 1 comprising preparing an aqueous gel of the polyacrylamide and the aqueous vehicle, incorporating the resultant gel into screened colloidal barium sulfate, homogenizing, and adjusted to the desired volume by the addition of the aqueous vehicle.

8. A method according to claim 8 wherein a thickening agent and an antifoam agent are added before homogenizing.

* * * * *

UNITED STATES PATENT OFFICE
CERTIFICATE OF CORRECTION

Patent No. 4,120,946　　　　　　　　Dated October 17, 1978

Inventor(s) Andre' QUEUILLE and Francoise HERBEMONT

It is certified that error appears in the above-identified patent and that said Letters Patent are hereby corrected as shown below:

Column 3, line 52, below "methyl parahydroxybenzoate" and before the horizontal line insert --propyl parahydroxybenzoate 0.022 g--
　　　line 53, insert before horizontal line --sweetened flavored aqueous excipient q.s.p. 240 g--;

Column 8, claim 8, line 1, change "8" to --7--.

*Signed and Sealed this*

*Twenty-fourth* Day of *April 1979*

[SEAL]

*Attest:*

RUTH C. MASON
*Attesting Officer*

DONALD W. BANNER
*Commissioner of Patents and Trademarks*